United States Patent [19]
de Paulis et al.

[11] Patent Number: 5,723,103
[45] Date of Patent: Mar. 3, 1998

[54] SUBSTITUTED BENZAMIDES AND RADIOLIGAND ANALOGS AND METHODS OF USE

[75] Inventors: Tomas de Paulis, Hermitage; Dennis E. Schmidt, Nashville; William Hewlett, Nashville; Michael H. Ebert, Nashville, all of Tenn.

[73] Assignee: Vanderbilt University, Nashville, Tenn.

[21] Appl. No.: 352,277

[22] Filed: Dec. 9, 1994

[51] Int. Cl.$^6$ .......................... A61K 51/00; A61M 36/14
[52] U.S. Cl. .......................... 424/1.85; 546/133
[58] Field of Search .................. 424/1.11, 1.37, 424/1.53, 1.65, 1.85, 9.1; 546/1.33

[56] References Cited

U.S. PATENT DOCUMENTS

| | | | |
|---|---|---|---|
| 4,605,652 | 8/1986 | Welstead, Jr. | 514/214 |
| 4,657,911 | 4/1987 | Imbert et al. | 514/272 |
| 4,717,563 | 1/1988 | Alphin et al. | 546/133 |
| 4,722,834 | 2/1988 | Teng et al. | 424/10 |
| 4,808,624 | 2/1989 | Monkovic et al. | 725/513 |
| 4,820,715 | 4/1989 | Monkovic et al. | 514/305 |
| 4,853,376 | 8/1989 | King | 546/133 |
| 4,863,919 | 9/1989 | Smith | 514/214 |
| 4,863,921 | 9/1989 | Youssefyeh et al. | 514/230.5 |
| 4,877,780 | 10/1989 | Vega-Noverola et al. | 514/161 |
| 4,888,353 | 12/1989 | Lednicer et al. | 514/422 |
| 4,892,872 | 1/1990 | Tahara et al. | 514/230 |
| 4,937,236 | 6/1990 | Vega-Noverola et al. | 514/161 |
| 5,017,580 | 5/1991 | Naylor et al. | 514/299 |
| 5,017,582 | 5/1991 | Donatsch et al. | 546/133 |
| 5,025,022 | 6/1991 | Naylor et al. | 514/305 |
| 5,142,069 | 8/1992 | Schmid | 549/462 |
| 5,154,913 | 10/1992 | dePaulis et al. | 424/1.1 |
| 5,189,041 | 2/1993 | Berger et al. | 514/288 |
| 5,202,318 | 4/1993 | Berger et al. | 514/211 |
| 5,202,333 | 4/1993 | Berger et al. | 514/296 |
| 5,225,407 | 7/1993 | Oakley et al. | 514/215 |
| 5,236,931 | 8/1993 | Jagdmann et al. | 514/305 |
| 5,240,957 | 8/1993 | Bengtsson et al. | 514/428 |

FOREIGN PATENT DOCUMENTS 2019042  5/1991  Spain.

OTHER PUBLICATIONS

Youssefyeh et al (1992) J. Med. Chem., vol. 35 No. 5, pp. 895–903, "Development of High Affinity 5–HT$_3$ Receptor Antagonists. Initial Structure Activity Relationship of Novel Benzamides".

Laporte et al. "Quantitative Autoradiographic Mapping of 5–HT$_3$ ... " *Synapse* 10(1):271–281, Jan., 1992.

Ponchant et al. "Synthesis of 5–[$^{125}$I]–Iodo–Zacopride ... " *J. Labelled Compounds and Radiphar.* 29(10):1147–1155, 1991 (no month or day given).

*Primary Examiner*—John Kight
*Assistant Examiner*—Dameron Jones
*Attorney, Agent, or Firm*—Needle & Rosenberg, P.C.

[57] ABSTRACT

This invention provides compounds of the formula I

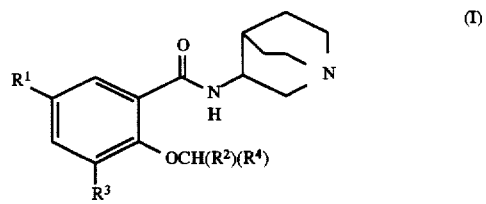

wherein, $R^1$, $R^2$, and $R^3$ are independently [a first halogen atom,] fluorine, chlorine, bromine, iodine, alkyl, alkenyl, alkynyl, alkoxy, alkenoxy, or alkynoxy, wherein $R^2$ and $R^3$ can also independently be H, wherein at least one of $R^1$, $R^2$, and $R^3$ is [a second halogen atom] fluorine, bromine, iodine or is substituted with [a second halogen atom,] fluorine, bromine or iodine and $R^4$ is H or lower alkyl. The invention also provides precursors of formula I, radioactive analogs of formula I, and methods of using the compounds for the identification of 5-HT-3 receptors and the detection and treatment of abnormal conditions associated therewith.

19 Claims, 1 Drawing Sheet

FIGURES

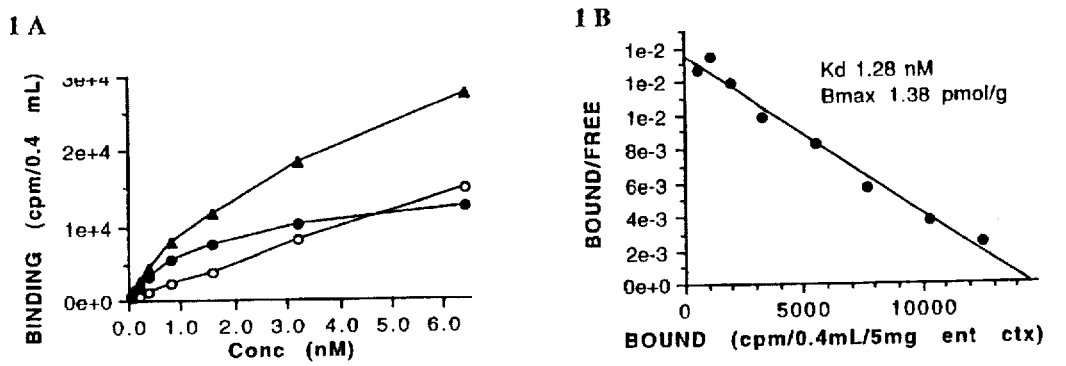

Figure 1A. Saturation of [$^{125}$I]-4 binding to rat entrorhinal cortical membranes.
Figure 1B. Scatchard analysis of [$^{125}$I]-4 binding.

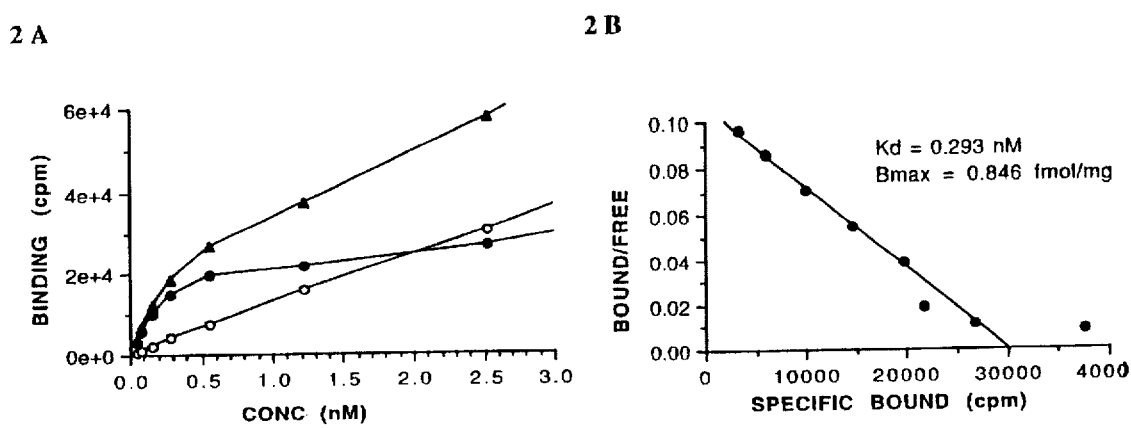

Figure 2A. Saturation of [$^{125}$I]-15 binding to rat whole brain excluding cerebellum.
Figure 2B. Scatchard analysis of [$^{125}$I]-15 binding.

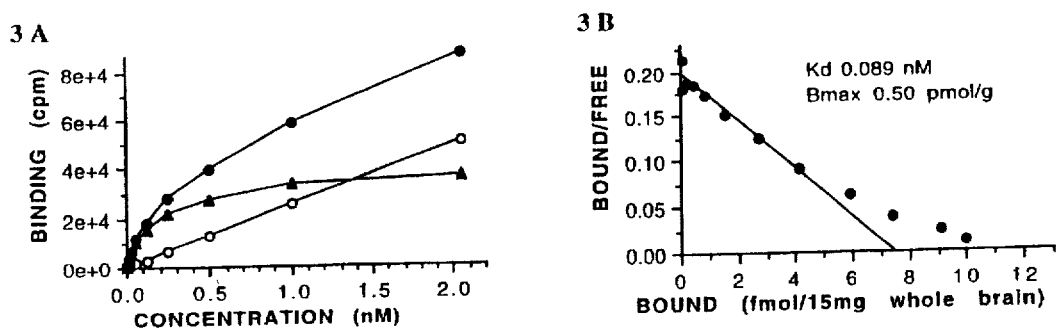

Figure 3A. Saturation of [$^{125}$I]-16 binding to whole rat brain excluding cerebellum.
Figure 3B. Scatchard analysis of [$^{125}$I]-16 binding.

SUBSTITUTED BENZAMIDES AND RADIOLIGAND ANALOGS AND METHODS OF USE

BACKGROUND OF THE INVENTION

1. Field of the Invention

The invention relates to substituted benzamides and radioligand analogs and methods of use.

2. Background Art

U.S. Pat. No. 5,154,913 to de Paulis et al. discloses radiolabeled compounds useful in imaging the Dopamine D-2 receptor of the brain. The compounds used to image the Dopamine D-2 receptor are disclosed by formula 1, which is a radioiodinated benzamide.

Ponchant et al., "Synthesis of 5-[$^{125}$I]-Iodo-Zacopride, A New Probe for 5-HT$_3$ Receptor Sites," *J. Lab. Cpds. and Radiopharm.*, Vol. XXIX, No. 10, pp. 1147–1155 (1991) discloses substituted 3-quinuclidinyl benzamides useful for 5-HT-3 serotonin receptor binding. These compounds can be radioiodinated.

U.S. Pat. No. 4,717,563 to Alphin et al., discloses a method of controlling emesis caused by administration of non-platinum anti-cancer drugs to warm-blooded animals utilizing particular N-3-quinuclidinyl benzamides and thiobenzamides.

U.S. Pat. No. 4,820,715 to Monkovic et al. discloses substituted 3-quinuclidinyl benzamide compounds which are asserted to be useful for the treatment of emesis, such as chemotherapy-induced emesis, and/or treatment of disorders related to impaired gastric motility.

None of the above-cited documents discloses or suggests the compounds or the methods of the invention as claimed herein. Thus, there is a need in the art to provide compounds and methods for the diagnostic and therapeutic utilities of the present invention.

SUMMARY OF THE INVENTION

This invention provides compounds of the formula I

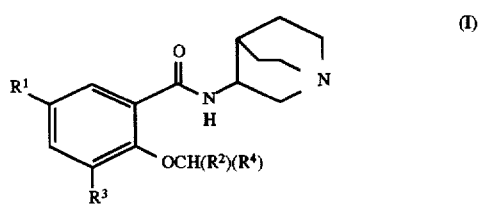

(I)

wherein, $R^1$, $R^2$, and $R^3$ are independently a first halogen atom, alkyl, alkenyl, alkynyl, alkoxy, alkenoxy, or alkynoxy, wherein $R^2$ and $R^3$ can also independently be H, wherein at least one of $R^1$, $R^2$, and $R^3$ is a second halogen atom or is substituted with a second halogen atom, and $R^4$ is H or lower alkyl.

The invention also provides compounds of the formula I, wherein $R^1$, $R^2$, and $R^3$ are independently a first halogen atom, alkyl, alkenyl, alkynyl, alkoxy, alkenoxy, or alkynoxy, wherein $R^2$ and $R^3$ can also independently be H, wherein at least one of $R^1$, $R^2$, and $R^3$ is a radioactive second halogen atom or is substituted with a radioactive second halogen atom, and $R^4$ is H or lower alkyl.

The invention also provides compounds of the formula I, wherein $R^1$, $R^2$, and $R^3$ are independently a first halogen atom, alkyl, alkenyl, alkynyl, alkoxy, alkenoxy, or alkynoxy, wherein $R^2$ and $R^3$ can also independently be H, wherein, at least one of $R^1$, $R^2$ and $R^3$ is a trialkyltin group or an aryl or alkyl sulfonyl group or at least one of $R^1$, $R^2$, and $R^3$ is substituted with a trialkyltin group or an aryl or alkyl sulfonyl group.

The invention also provides pharmaceutical compositions containing the compounds of the instant invention and methods of using the compounds for the identification of 5-HT-3 receptors and the detection and treatment of abnormal conditions associated therewith.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

FIG. 1A shows the saturation of [$^{125}$I]-4 (TDP 960 from Table I) binding to rat entrorhinal cortical membranes. In all FIGS. 1–3, triangles represent total binding, open circles represent non-specific binding, and darkened circles represent specific binding.

FIG. 1B shows the scatchard analysis of [$^{125}$I]-4 binding.

FIG. 2A shows the saturation of [$^{125}$I]-15 (TDP 984 from Table I) binding to rat whole brain excluding cerebellum.

FIG. 2B shows the scatchard analysis of [$^{125}$I]-15 binding.

FIG. 3A shows the saturation of [$^{125}$I]-16 (TDP 1040 from Table I) binding to whole rat brain excluding cerebellum.

FIG. 3B shows the scatchard analysis of [$^{125}$I]-16 binding.

DETAILED DESCRIPTION OF THE INVENTION

The present invention may be understood more readily by reference to the following detailed description of preferred embodiments of the invention and the Examples included therein and to the Figures and their previous and following description.

Before the present compounds, compositions and methods are disclosed and described, it is to be understood that this invention is not limited to specific synthetic methods, specific pharmaceutical carriers, or to particular pharmaceutical formulations or administration regimens, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a compound" includes mixtures of compounds, reference to "a pharmaceutical carrier" includes mixtures of two or more such carriers, and the like.

In this specification and in the claims which follow, reference will be made to a number of terms which shall be defined to have the following meanings:

The term "alkyl" as used herein refers to a branched or unbranched saturated hydrocarbon group of one to six carbon atoms, such as methyl, ethyl, n-propyl, isopropyl, n-butyl, isobutyl, t-butyl, pentyl, hexyl, and the like. The term "lower alkyl" intends an alkyl group of from one to three carbon atoms. Alkenyl and lower alkenyl are the same as alkyl and lower alkyl, respectively, except that at least one double bond, and therefore at least two carbon atoms, is present. Alkynyl and lower alkynyl similarly are the same as alkyl and lower alkyl, respectively, except that at least one triple bond, and therefore at least two carbon atoms, is present.

The terms "alkoxy," "alkenoxy," and "alkynoxy" as used herein intends an alkyl, alkenyl, or alkynyl group, respectively, bound through a single, terminal ether linkage; that is, an alkoxy, ankenoxy, or alkynoxy group may be defined as —OR where R is alkyl, alkenyl, or ankynyl, respectively, as defined above. A "lower alkoxy" group intends an alkoxy group containing from one to three carbon atoms. A "lower alkenoxy" or "lower alkynoxy" intends an alkenoxy or alkynoxy group, respectively, containing from two to three carbon atoms.

Halogen atom as used herein includes F, Cl, Br, and I.

By the term "effective amount" of a compound as provided herein is meant a nontoxic but sufficient amount of the compound to provide the desired effect. As will be pointed out below, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount may be determined by one of ordinary skill in the art using only routine experimentation.

The present invention provides a compound of the formula I

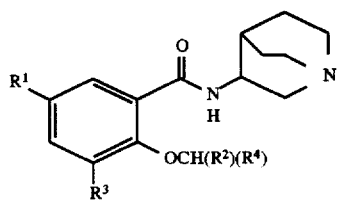
(I)

wherein, $R^1$, $R^2$, and $R^3$ are independently a first halogen atom, alkyl, alkenyl, alkynyl, alkoxy, alkenoxy, or alkynoxy, wherein $R^2$ and $R^3$ can also independently be H, wherein at least one of $R^1$, $R^2$, and $R^3$ is a second halogen atom or is substituted with a second halogen atom, and $R^4$ is H or lower alkyl. The alkyl, alkenyl, alkynyl, alkoxy, alkenoxy, and alkynoxy groups can be substituted or unsubstituted with one or more halogen atoms, such as F, Cl, Br, or I. The invention also provides that the carbon atom of the 3-quinuclidinyl moiety attached to the amide nitrogen can have the S or R configuration.

In alternative embodiments of this and the compounds below, at least one of $R^1$, $R^2$, and $R^3$ is a radioactive second halogen atom or is substituted with a radioactive second halogen atom. Radioactive compounds of the present invention are generally useful for detection and imaging, discussed in more detail below. Preferably, the substitution of the radioactive second halogen atom is on the terminal portion of $R^2$ or $R^3$. The radioactive second halogen atom is preferably a radioactive isotope of fluorine, bromine, or iodine, preferably including $^{18}F$, $^{75}Br$, $^{76}Br$, $^{77}Br$, $^{123}I$, $^{124}I$, $^{125}I$, or $^{131}I$, even more preferably $^{18}F$, $^{76}Br$, or $^{123}I$.

The invention provides that the first halogen atom can be fluorine, chlorine, bromine, or iodine, and in another embodiment, the second halogen atom can be fluorine, bromine, or iodine. The invention provides in a preferred embodiment that the alkyl, alkenyl, alkynyl, alkoxy, alkenoxy, and alkynoxy are lower alkyl, lower alkenyl, lower alkynyl, lower alkoxy, lower alkenoxy, and lower alkynoxy, respectively.

For the non-radioactive compounds, in a preferred embodiment, $R^1$ is a first halogen atom; $R^2$ is H, lower alkyl unsubstituted or substituted with a second halogen atom, or lower alkenyl unsubstituted or substituted with a second halogen atom; $R^3$ is a second halogen atom or lower alkoxy unsubstituted or substituted with a second halogen atom; and $R^4$ is H or a methyl group.

In an even more preferred embodiment, the carbon atom of the 3-quinuclidinyl moiety attached to the amide nitrogen has the S or the R configuration and $R^4$ is H, and $R^1$ is I, $R^2$ is H, and $R^3$ is $OCH_3$; $R^1$ is Cl, $R^2$ is $CH_2F$, and $R^3$ is $OCH_3$; $R^1$ is Cl, $R^2$ is CH=CHI, and $R^3$ is $OCH_3$; $R^1$ is Cl, $R^2$ is H, and $R^3$ is I; $R^1$ is Cl, $R^2$ is $CH_2F$ and $R^3$ is I; $R^1$ is Cl, $R^2$ is H, and $R^3$ is $OCH_2CH_2F$; $R^1$ is F, $R^2$ is H, and $R^3$ is I; or $R^1$ is Cl, $R^2$ is H, and $R^3$ is $OCH_2CH$=CHI.

For the radioactive compounds, in a preferred embodiment, $R^1$ is a first halogen atom or a radioactive second halogen atom; $R^2$ is H, lower alkyl unsubstituted or substituted with a non-radioactive second halogen atom or a radioactive second halogen atom, or lower alkenyl unsubstituted or substituted with a non-radioactive second halogen atom or a radioactive second halogen atom; $R^3$ is a non-radioactive second halogen atom or a radioactive second halogen atom or lower alkoxy unsubstituted or substituted with a non-radioactive second halogen atom or a radioactive second halogen atom; and $R^4$ is H or a methyl group.

In an even more preferred embodiment, the carbon atom of the 3-quinuclidinyl moiety attached to the amide nitrogen has the S or the R configuration and $R^4$ is H, and $R^1$ is I, $R^2$ is H, and $R^3$ is $OCH_3$; $R^1$ is Cl, $R^2$ is $CH_2F$, and $R^3$ is $OCH_3$; $R^1$ is Cl, $R^2$ is CH=CHI, and $R^3$ is $OCH_3$; $R^1$ is Cl, $R^2$ is H, and $R^3$ is I; $R^1$ is Cl, $R^2$ is $CH_2F$ and $R^3$ is I; $R^1$ is Cl, $R^2$ is H, and $R^3$ is $OCH_2CH_2F$; $R^1$ is F, $R^2$ is H, and $R^3$ is I; or $R^1$ is Cl, $R^2$ is H, and $R^3$ is $OCH_2CH$=CHI, wherein at least one of I or F is radioactive.

The invention also provides a compound of the formula I,

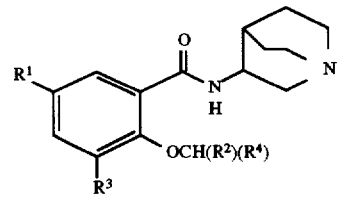
(I)

wherein, $R^1$, $R^2$, and $R^3$ are independently a first halogen atom, alkyl, alkenyl, alkynyl, alkoxy, alkenoxy, or alkynoxy, wherein $R^2$ and $R^3$ can also independently be H, wherein, at least one of $R^1$, $R^2$ and $R^3$ is a trialkyltin group or an aryl or alkyl sulfonyl group or at least one of $R^1$, $R^2$, and $R^3$ is substituted with a trialkyltin group or an aryl or alkyl sulfonyl group. A trialkyltin group can be used as the precursor for iodine and bromide halogenation and an aryl or alkyl sufonyl group can be used as the precursor for fluorine halogenation.

The invention also provides a composition for the treatment of an abnormal conditions associated with an altered 5-HT-3 receptor binding, or with altered neurotransmitter receptor function regulated by 5-HT-3 receptors, in an individual comprising a therapeutically effective amount of the above compounds and a pharmaceutically acceptable carrier. Thus, the invention also provides a method of treating an abnormal condition associated with altered 5-HT-3 receptor function, or with altered neurotransmitter receptor function regulated by the 5-HT-3 receptors in an individual mammal comprising administering to the individual a therapeutic amount of the above compounds.

Depending on the intended mode of administration, the compounds of the present invention can be in pharmaceutical compositions in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. Typically, the compound will be in a liquid. In a preferred embodiment, the compound is purified by HPLC, filtered through a sterile filter and administered intravenously to the individual. The compositions will include, as noted above, an effective amount of the compound in combination with a pharmaceutically acceptable carrier and, in addition, may include other medicinal agents, pharmaceutical agents, carriers, adjuvants, diluents, etc. By pharmaceutically acceptable it is meant a material that is not biologically or otherwise undesirable, i.e., the material may be administered to an individual along with the compound without causing any undesirable biological effects or interacting in a deleterious manner with any of the other components of the pharmaceutical composition in which it is contained.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc. an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*.

The compositions and methods of treatment and diagnosis disclosed herein contemplate that the abnormal condition or disorder is selected from the group consisting of gastric hypermotility, nausea, vomiting, bulemic, anorectic, and migraine conditions, and anxiety, personality, substance abuse, psychotic, schizophrenic, and cognitive disorders; as defined by DSM III and DSM IV and ICD or othoer diagnostic criteria. *Diagnostic and Statistical Manual of Mental Disorders IIIR*, American Psychiatric Assoc., Washington, D.C. (1984); *Diagnostic and Statistical Manual of Mental Disorders IV*, American Psychiatric Assoc., Washington, D.C. (1994)

A discussion with references of the conditions which can be treated with the present compounds may be found in *5-Hydroxytryptamine-3 Receptor Antagonists*, (King F. D., Jones, B. J., Sanger, G. J., eds.), CRC Press, Ann Arbor (1994) or *Central and peripheral 5-HT-3 Receptors*, (Hamon H., ed. ), Academic Press, Boston (1992).

The compounds of the present invention can be used to treat nausea and vomiting. For example, Ondansetron (Zofran) has been approved by the FDA for use to alleviate the nausea and vomiting that occurs as a result of treatment of certain cancers (esp. testicular cancer) with cis-platin.

Cis-platin causes a release of serotonin from the enterochromafin cells in the gut. 5-HT-3 antagonists may block actions of serotonin in the gut. In addition, actions of blood-borne serotonin promoting nausea and vomiting via an interaction with 5-HT-3 receptors in a circumventricular organ, the area postrema, which is accessible to blood-born substances may be blocked with this agent. 5-HT-3 antagonists may also act to alleviate nausea and vomiting via a central action in the medulla. Other 5-HT-3 antagonists continue to be evaluated in a variety of animal and clinical trials designed to evaluate their potential or clinical efficacy as antiemetic agents.

See generally, Addelman, M., Erhickman, C., and Fine, S., Phase I/II trial of graniserton: a novel 5-hydroxytryptamine antagonist for the prevention of chemotherapy-induced nausea and vomiting. *J. Clin. Oncol.*, Vol. 8, pp. 337–341 (1990); Andrews, P. L. R. and Bhandari, P., "The 5-hydroxytryptamine receptor antagonists as antiemetics: preclinical evaluation and mechanism of action." *Eur. J. Cancer*, Vol. 29A, pp. 511–516 (1993); Beck, T. M., Haskelh, P. J., Madajewicz, S. et al., "Stratified, randomized, double-blind comparison of intravenous ondansetron administered as a multiple-dose regimen versus two single-dose regimens in the prevention of cisplatin-induced nausea and vomiting," *J. Clin Oncol.*, Vol. 10, pp. 1969–1975 (December 1992); Bodner, M., and White, P. F., "Antiemetic efficacy of ondansetron after outpatient laparoscopy," *Anaesth. Analg.*, Vol. 73, pp. 250–254 (1991); Boyce, M. J. and Orwin, J. M., "MDL 72222: A review of clinical studies," *Perugia Int. Conf., III, Proc.*, Vol. 88 (1990); Boyce, M. J., Hinze, C., Haegele, K. D., O'Grady, P., and Busch, B., "Early clinical studies with MDL 73147EF, a new and potent selective 5-HT-3, receptor antagonist," *Perugia Int. Conf. III, Proc.*, Vol. 89 (1990); Bregni, M., Siena, S., Di Nicola, M., Bonadonna, G., and Giannin, A. M., "Tropisetron plus haloperidol to ameliorate nausea and vomiting associated with high-dose alkylating agent cancer therapy," *Eur. J. Cancer*, Vol. 27, pp. 561–565 (1991); Carmichael, J., Cantwell, B. M. J., Edwards, C. M., Rapeport, W. G., and Harris, A. L., "Prevention and amelioration of cisplatinum-induced nausea and vomiting by BRL 43694, a selective 5-HT, receptor antagonist: results of an open dose ranging study," *Br. Med J.*, Vol. 297, pp. 110–111 (1988); Cassidy, J., Raina, V., Lewis, C., Adams, L., Soukop, M., Rapaport, W. G., Zussman, B. D., Rankin, E. M., and Kaye, S. B., "Pharmacokinetics and anti-emetic efficacy of BRL 43694, a new selective 5HT, antagonist," *Br. J. Cancer*, Vol. 58, pp. 651–653 (1988); Costall, B., Domeney, A. M., Naylor, R. J., and Tattersall, F. D., "5-hydroxytryptamine M-receptor antagonism to prevent cisplatin-induced emesis," *Neuropharmacology*, Vol. 25, pp. 959–961 (1986); Cubeddu, L. X., Hoffman, I. S., Fuenmayor, N. T., and Finn, A. L., "Efficacy of ondansetron and the role of secrotonin in cisplatin-induced nausea and vomiting," *N. Engl. J. Med.*, Vol. 322, pp. 810–816 (1990); Cunningham, D., Turner, A., Hawthorn, J. and Rosin, R. D., "Ondanestron with and without dexarnethasone to treat chemotherapy," *Lancet*, Vol. 1, p. 1323 (1989); Fraschini, G., Ciocciola, A., Esparza, L., Templeton, D., Homes, F. A., Walters, R. S. and Hortogagyt, G. N., "Evaluation of three oral dosages of ondansetron in the prevention of nausea and emesis associated with cyclophosphamide-doxombiein chemotherapy," *J. Clin. Oncol.*, Vol. 9, pp. 1268–1274 (1991); Fukuda, T., Setoguchi, M., Inaba, K., Shoji, H., and Tahara, T., "The antiemetic profile of Y-25130, a new selective 5-HT, receptor antagonist," *Eur. J. Pharmacol.*, Vol. 196, pp. 299–305 (1991); Goldberg, M. J. and Cerimele, B. J., "Effect of zatosetron (LY 277359), a serotonergic (5-HT-3)antagonist on ipecae-induced emesis in healthy men," *Clin. Pharm. Ther.*, Vol. 49, p. 171 (1991); Hunter, A. E., Prentice, H. G., Pothecary, K., Coumar, A., Collis, C., Upward, J., Murdoch, R., Gandhl, L., Harmon, M., Butler, M., and Wells, J., Granisetron, "A selective 5-HT, receptor antagonist, for the prevention of radiation-induced emesis, during total body irradiation," *Bone Marrow Transpl.*, Vol. 7, pp. 439–441 (1991); Jones, A. L., Hill, A. S., Soukop, M., Hutcheson, A. A., Cassidy, J., Kaye, S. B., Sikora, K., Carney, D. N., and Cunningham, D., "Comparison of dexamethasone and ondansetron in the prophylaxis of emesis induced by moderately emetogenic chemotherapy," *Lancet*, Vol. 338, pp. 483–487 (1991); Kris, M. G., Cralla, R. J., Clark, R. A., and Tyson, L. B., "Phase II Trials of the serotonin antagonist GR 38032F for the control of vomiting caused by cisplatin," *J. Natl. Cancer Inst.*, Vol. 81, pp. 42–46 (1989); Monkovic, I. and Glys, J. A., "Developments in the anti-emetic area: chemistry, pharmacology and therapy," *Prog. Med. Chem.*, Vol. 27, pp. 297–323 (1990); Priestman, T. J., "Clinical studies with ondansetron in control of radiation-induced emesis," *Eur. J. Cancer Clin. Oncol.*, Vol. 25, (Suppl. 1), pp. S29–33 (1989); Viner, C. V., Selby, P. J., Zulian, G. B., Gore, M. E., Butcher, M. E., Wooton, C. M., and McElwain, T. J., "Ondanstron—a new safe and effective anti-emetic in patients receiving high-does melphalan," *Cancer Chemo., Pharmacol.*, Vol. 24, p. 449–453 (1990).

Additionally, ample supplies of serotonin in the gut occurring in close association with 5-HT-3 receptors suggest that they have a functional role in controlling visceral function. 5-HT-3 antagonists have been tested in a variety of other intestinal disorders, such as (a) visceral pain, (b) irritable bowel syndrome, (c) treatment of diarrhea, and (d) treatment of carcinoid syndrome. See generally, Maxton, D. G., Haigh, C. C. & Whorwell, P. J., "Clinical trial of ondansetron a selective antagonist in irritable bowel syndrome (IBS)," *Gastroenterol.*, Vol. 100, p. A468 (1991); Prior, A. & Read, N. W., "Reduction of rectal sensitivity and post-prandial motility by granisetron, a 5-HT$_3$ receptor antagonist in patients with irritable bowel syndrome (IBS)," *Gut*, Vol. 31, p. A1174 (1990); Stacher, G., Gaupmann, G., Schneider, C., Stacher-Janotta, G., Steiner-Mittelbach, G., Abatzi, Th.-A and Steinringer, H., "Effects of a 5-hydroxytryptamine$_3$ receptor antagonist (ICS 205–930) on colonic motor activity in healthy men," *Br. J. Clin, Pharmacol.*, Vol. 28, pp. 315–322 (1989); Steadman, C. J., Talley, N. J., Phillips, S. F. & Mulvihill, C., "Trial of a selective serotonin type 3 (5-HT3) receptor antagonist ondansetron (GR38032F) in diarrhoea predominant irritable bowel syndrome (IBS)," *Gastroenterol.*, Vol. 98, p. A394 (1990); and, Talley, N. J., Phillips, S. F., Haddad, A., Miller, L. J., Twomey, C., Zinsmeister, A. R. & Ciociola, A., "Effect of selective 5-HT$_3$ antagonist (GR 38032F) on small intestinal transit and release of gastrointestinal peptides," *Dig. Dis. Sci.*, Vol. 134, pp. 1511–1515 (1989).

The fact that 5-HT is involved in anxiety has been known for a number of years, based on broad evidence that stimulating 5-HT function enhances anxiety while inhibiting 5-HT function reduces it. However, the exact mechanisms whereby serotonergic function is related to anxiety is poorly understood. There are numerous animal models for investigating anti-anxiety effects, but the mechanistic rationale for these tests are strongly biased toward investigation of benzodiazepine-type anxiolytics and their suitability for investigation of serotonergic agents is variable. Only quite recently have 5-HT-3 antagonists been tested in these paradigms and these studies indicate that 5-HT-3 antagonists constitute a new class of pharmacological agents for treating anxiety-related disorders. Classes of anxiety-related disorders (or their most relevant animal models) that have been shown to be sensitive to 5-HT-3 specific agents are as follows: (a) Generalized Anxiety Disorder (non-specific animal models of anxiety, models relating to anti-CCK effects); (b) Obsessive complusive disorder; OCD (animals models related to risk aversion); (c) Social phobia (animal models relating to social interaction tests). See generally, Gao, B. and Cutler, M. G., "Anxialytic-like effects in mice induced by the 5-HT-3, receptor antagonist, BRL 46470A," *Br. J. Pharmacol.*, Vol. 106, p. 147 (1992a); Abuzzahab, F. S., "Ondansetron: A novel anti-anxiety agent," *New Concepts in Anxiety*, Briley, M. and File, S. E., Eds., Macmillan, Basingstoke, pp. 185–189 (1991); and, Borsini, F., Templeton, D., Turconi, M., Nicola, M., Schiantarelli, P., and Donetti, A., "Anxiolytic profile of a new structural class of 5-HT, antagonists," *Psychopharmacology*, Vol. 101, p. S7 (1990).

Several classes of personality disorder are related to avoidance of situations that are incorrectly perceived by the subjects as involving risk and/or causing undue or abnormal anxiety. Evidence indicates that these disorders therefore will also respond favorably to 5-HT-3 antagonists. The most prevalent of these disorders and their relevant animal models are as follows: (a) Obsessive-compulsive personality (animals models related to risk aversion) (see above); (b) Schizoid (animal models that test social interactions or to risk aversion); and, (c) avoidant (animal model related to risk aversion). For examples of these therapies, see generally, Lader, M. H., "Ondansetron in the treatment of anxiety," *Biological Psychiatry*, Racagni, G., Bunello, N., and Fukuda, T., Eds., Excerpta Medica, Amsterdam, Vol. 2, pp. 885–887 (1991); Pecknold, J. C., "Platelet [$^3$H] paroxctine and [3H] imipramine binding in a zacopride treated patients with generalized anxiety disorder: preliminary results," paper presented at the Int. Symp. New Concepts in Anxiety, Castres, FRANCE (April 1990); Schweizer, E. and Rickels, K., "Serotonergic anxiolytics: a review of their clinical efficacy, in 5-HT$_{1a}$ Agonists, 5-HT$_3$, Antagonists and Benzodiazepines: Their Comparative Behavioural Pharm., Rodgers, R. J. and Cooper, S. J., Eds., Wiley, Chichester, pp. :365–976 (1991).

It is widely accepted that most forms of schizophrenia are related to dopaminergic hyperfunction in specific brain regions. It has now been demonstrated that alteration of serotonergic function in the limbic system can modify dopaminergically-mediated behaviors. Important limbic areas such as nucleus accumbens and amygdala have comparatively high concentrations of 5-HT-3 receptors and there is evidence that these receptors play a permissive role in regulation of dopaminergic function. Thus, antagonism of these permissive receptors as a means of reducing limbic dopaminergic function has a sound rationale and 5-HT-3 antagonists are under active investigation in animal models of mesolimbic dopaminergic hyperfunction and in treatment of schizophrenia. In addition to attenuation of dopminergic function, the anxiolytic and cognitive enhancing properties of 5-HT-3 antagonists can have additional therapeutic benefits in the treatment of schizophrenia. The following references generally describe these studies. Costall, B., Bomeney, A. M., Kelly, M. D., and Naylor, R. J., "Potential antischizophrenic activity of serotonin receptor antagonists," *Psychopharmacology*, Vol. 96, p. 84 (1988); Costall, B., Domeney, A. M., and Naylor, R. J., "5-HT-3 receptor antagonists attenuate dopamine-induced hyperactivity in the rat," *NeuroReport.*, Vol. 1, pp. 77–80 (1990); Fozard, J. R., Ed. Oxford Medical Publications, Oxford, pp.

354–376 (1989); Jiang, L. H., Ashby, C. R., Kasser, R. J. and Wang, R .Y., "The effect of intraventricular administration of the 5-HT-3 receptor agonist 2-methylscrotonin of the release of dopamine in the nucleus accumbens: an in vivo chronocoulometric study," *Brain Res.*, Vol. 513, pp. 156–160 (1990); Meltzer, H. Y., "Clinical studies on the mechanism of action of clozapine: the dopamine:serotonin hypothesis of schizophrenic," *Psychopharmacology*, Vol. 99, p. S18–S27 (1989); and, Sorensen, S. M., Humphreys, T. M., and Palfreyman, M. G., "Effect of acute and chronic MDL 73147EF, a 5-HT-3 receptor antagonist on A9 and A10 dopamine neutrons," *Eur. J. Pharmacol.*, Vol. 163, pp. 115–118 (1989).

It has been known for many years that enhanced serotonergic function will impair animal performance in learning and memory paradigms and that antagonism of serotinergic function can facilitate such behavior. Recent studies have shown that 5-HT-3 receptors mediate inhibition of acetylcholine release in cortical and limbic brain areas and that acetycholine release is increased by 5-HT-3 antagonists. Thus, 5-HT-3 antagonists can modify cognitive performance by enhancing cholinergic function in key hippocampal and cortical brain regions. The following references describe these studies. Bianchi, C., Sinisalchi, A., and Beani, L., "5HTta angonists increase 5-HT-3 agonists decrease acetylcholine efflux from the cerebral cortex of freely-moving guinea-pigs," *Br. J. Pharmacol.*, Vol. 101, pp. 448–452 (1990); Bowen, D. M., Smith, C. B., White, P., and Davison, A. N., "Biochemical assessment of serotonergic and cholinergic dysfunction and cerebral atrophy in Alzheimer's disease," *J. Neurochem.*, Vol. 41, pp. 266–272 (1983); Cook, T. and Lakin, M., "Effects of ondansetron in age-associated memory impairment," *5th World Cong. Biological. Psychiatry, Satellite Symp.* The Role of Ondansetron, a Novel 5-HT3 antagonist in the Treatment of psychiatric Disorders, pp. 21–23 (1991); Lawlor, B. A., Stunderland, T., Mellow, A. M., Hill, J. L., Newhouse, P. A., and Murphy, D. L., "A preliminary study of the effects of intravenous m-chlorophenylpiperazine, a serotonin agonist, in elderly subjects," *Biol. Psychiatr.*, Vol. 25, pp. 679–686 (1989b); File, S. E., Preclinical studies of the mechanisms of anxiety and its treatment. In *Neurobiology of Panic Disorder*, (ed. Ballenger, J. C.), pp. 31–48. New York, Alan R. Liss; Mos. J., Heyden, J. V. d. & Olivier, B., (1989), Behavioural effects of 5-HT-3 antagonists in animal models for aggression, anxiety and psychosis. In *Behavioural Pharmacol. of 5-HT* (eds Bevan, P., Cools, R. & Archer, T.), pp 389–395, New Jersey, Lawrence Erlbaum Assoc.; and, Young, R. & Johnson D. A., "Comparative effects of zacopride, GR38032F (ondansetron), buspirone, and diazepam in the mouse light/dark exploratory model," *Soc. Neurosci. Abstr.*, Vol. 14, p. 207 (1988).

Unlike drugs that specifically treat a single class of drug abuse, for example, methandon for treatment of narcotic addiction, the developing hypothesis for the use of 5-HT-3 antagonists is based on their ability to reduce or abolish the reward properties of such drugs. It is thought that an increase in CNS-mediated reward effects, the "feel good" part of being high, is an important aspect of addiction and relapse from termination of abuse. Because increased reward produced by all drugs with abuse potential are thought to be related to increased dopaminergic function in critical brain regions that also contain 5-HT-3 receptors, treatment of addiction with 5-HT-3 antagonists transcends specific drug classes and can be used with a variety of different drugs of abuse. The proposed mechanism of action is thought to be based on the ability of 5-HT-3 antagonists to reduce dopaminergic function.

In addition, dopaminergic neurotransmission and its attendant behavioral reinforcement may play a role in maintaining other maladaptive behaviors such as those associated with sexual paraphiliac, eating, and impulse control disorders. As such, it follows that reductions in dopaminergic communication associated with administration of 5-HT-3 antagonists should have the effect or reducing these maladaptive behaviors, and therefore should be effective in the treatment of these disorders.

A common feature of withdrawal from addiction is a significant increase in anxiety. Because 5-HT-3 antagonists can be used in treating anxiety-related disorders, they also can be used in ameliorating the aversive effects of withdrawal and, therefore, make success more likely. See generally, Montgomery, A. M. J., "The Effect of a 5-HT-3 Receptor Antagonist, Ondausetron, On Brain Stimulation Reward, and Its Interaction With Direct and Indirect Stimulants of Central Dopminergic Transmission," *J. Neural Transm.* [*Gen. Sect.*], Vol. 91, pp. 1–11 (1993); Acquas, E., Carboni, E., Garau, L., and Di Chiara, G., "Blockage of acquisition of drug conditioned place aversion by 5-1-117-3, antagonists," *Psychopharmacology*, Vol. 100, pp. 459–463 (1990); Barry, J. M., Costall, B., Kelley, M. E., and Naylor, R. J., "Withdrawal syndrome following subchronic treatment with anxiolytic agents," *Pharmacol. Bioehcm. Behav.*, Vol. 27, pp. 239–245 (1987); Bilsky, E. J. and Reid, L. D., "MDL 72222, a serotonin 5-HT$_3$ receptor antagonist, blocked MDMA's ability to establish a conditioned place preference," *Pharmacol. Biochem. Behav.*, Vol. 39, pp. 509–512 (1991); Costall, B., Jones, B. J., Kelly, M. D., Naylor, R. J., Onaivl, E. S. and Tyers, M. D., "Ondansetron inhibits a behavioural consequence of withdrawing from drugs of abuse," *Pharmacol. Biochem. Behav.*, Vol. 36, pp. 339–344 (1990a); Goudie, A. J., and Leathley, M. J., "Effects of the 5-HT$_3$, antagonist GR 38032F (ondansetron) on benzodiazepine withdrawal in rats," *Eur. J. Pharmacol.*, Vol. 185, pp. 179–186 (1990); Higgins, G. A., Nguyen, P., Joharchi, N., and Sellers, E. M., "Effects of 5-HT$_3$ receptor antagonist on behavioural measures of naloxone-precipitated opioid withdrawal," *Psychopharmacology*, Vol. 105, pp. 322–328 (1991b); Tricklebank, M. D., "Interactions between dopamine and 5-HT$_3$ receptors suggest new treatments for psychosis and drug addiction," *Trends Pharmac. Sci.*, Vol. 10, pp. 127–129 (1989); van der Hoek, G. A. and Cooper, S. J., "Evidence that ondansetron, a selective 5-HT$_3$ antagonist reduces cocaine's psychomotor stimulant effects in the rat," *Psychopharmacology*, Vol. 101, p. 414P (1990a); and, Wozniak, K. M., Pert, A., and Linnoila, M., "Antagonism of 5-HT$_3$ receptors attenuates the effects of ethanol on extracellular dopamine," *Eur. J. Pharmacol.*, Vol. 187, pp. 287–290 (1990).

There is an extensive literature that implicates multiple aspects of serotonegic function to pain, or nociception, in humans. One aspect of the involvement of serotonin receptors in pain has been evidence that 5-HT-3 antagonists are effective in treating acute migraine headache. See generally, Fozard, J. R., "5-HT in migraine: evidence from 5-HT receptor antagonists for a neuronal actiology", *Migraine: a Spectrum of Ideas, Sandler*, M., and Collins, G. Eds., Oxford Medical Publishers, Oxford University Press, Oxford, UK, pp. 128–140 (1990); Rowat, B. M. T., Merrill, C. F., Davies, A., and South, V., "A double-blind comparison of granisetron and piacebo for the treatment of acute migraine in the emergency department," *Cephalalgia*, Vol. 11, pp. 207–23 (1991); Couturier, E. G. M., Hering, R., Foster, C. A. & Steiner, T. J., "First clinical study of the selective 5-HT$_3$ antagonist, granisetron (BRL 43694), in the acute treatment of migraine headache," *Headache*, Vol. 31, pp. 296–297 (1991); Fozard, J. R., Loisy, C. & Tell, G., "Blockade of neuronal 5-hydroxytryptamine receptors with MDL 72222, A novel approach to the symptomatic treatment of migraine," *Proc. 5th Int. Migraine Symp.*, (ed. Clifford-Rose, F.), Basel, Karger, pp. 265, 272 (1985); and, Loisy, C., Beorchia, S., Centonc, V., Fozard, J. R., Schechter, P. and Tell, G. P., "Effects on migraine headache of MDL 72222 an antagonist of neuronal 5-HT receptors, Double-blind, placebo-controlled study," *Cephalalgia*, Vol. 5, pp. 79–82 (1985).

In one embodiment of the invention, the compounds used for the treatment of abnormal conditions such as those listed above can have the carbon atom of the 3-quinuclidinyl moiety attached to the amide nitrogen in the R configuration. The use of similar compounds in either the R or S isomer forms has been shown to have differing effects. For example, zacopride is a potent 5-HT-3 receptor antagonist which exists in two stereoisometric forms. (S)-zacopride displays the highest affinity for this receptor ($K_i$ 0.3 nM) and is an effective antiemetic agent. The less active enantiomer, (R)-zacopride displays ten times lower affinity for the 5-HT-3 receptor, but shows cognitive-enhancing properties in animal behavioral models. (R)-zacopride is also able to block drug-induced anxiety whereas the (S)-form is inactive. See generally, Emerit et al., *J. Neurochem.*, Vol. 60, pp. 2059–67 (1993); Barnes, N. M., Costall, B., Ge, J., Kelly, M. E. and Naylor, R. J., "The interaction of R(+)- and S(-)-zacopride with PCPA to modify rodent aversive behavior," *Eur. J. Pharmacol.*, Vol. 218, pp. 15–25 (1992); Kidd, E., de Vendegies I. B., Levy, J. C., Hamon, M. and Gozlan, H., "The potent 5-HT3 receptor antagonist (R)-zacopride labels an additional high affinity site in the central nervous system," *Eur. J. Pharmacol.*, Vol. 211, pp. 133–136 (1992); and, Waeber, C., Pinkus, L. M., and Palacios, J. M., "The (S)-isomer of [$^3$H]zacopride labels 5-HT$_3$ receptors with high affinity in rat brain," *Eur. J. Pharmacol.*, Vol. 181, pp. 283–287 (1990).

Typically, the (S)-forms are thus preferred imaging agents (when radiolabeled) of the 5-HT-3 receptor. Typically, the (R)-forms are preferred anxiolytic agents. Both forms are potential cognitive-enhancing agents that could be useful in ameliorating the symptoms of Alzheimer's disease, for example.

The invention also provides a method of identifying the presence of 5-HT-3 receptors in a sample comprising a. contacting the sample with one of the radiolabeled compounds; and, b. detecting binding between the compound and 5-HT-3 receptors, thereby identifying the presence of 5-HT-3 receptors in the sample. When the detecting step is performed in vitro, the detecting technique can be selected from the group consisting of autoradiography and receptor binding.

The techniques for performing an in vitro receptor binding assay may be found in Kilpatrick, G. J., Jones, B. J., and Tyers, M. D., *Nature*, Vol. 330, pp. 746–748 (1987); and in Kilpatrick, G. J., Butler, A., Hagan, R. M., Jones, B. J., and Tyers, M. D., "[$^3$H] GR67330, a very high affinity ligand for 5-HT$_3$ receptors," *Nauyn-Schmiedeberg's Arch Pharmacol.*, Vol. 342, pp. 22–30 (1990). An example of the techniques for performing autoradiography may be found in LaPorte et al., *Synapse*, Vol. 10, pp. 271–281 (1992).

The invention also provides a method of identifying the location of 5-HT-3 receptors in an individual comprising a. administering to the individual one of the radiolabeled compounds; and, b. detecting binding between the compound and 5-HT-3 receptors, thereby identifying the presence of 5-HT-3 receptors in the individual. When the detecting step is performed in vivo, the detecting technique can be selected from the group consisting of single photon emission tomography (SPET) and positron emission tomography (PET), for example.

The techniques for performing a SPET assay may be found in Kessler, R. M., Mason, N. S., Votaw, J. R., de Paulis, T., Clanton, J. A., Ansari, M. S., Schmidt, D. E., Manning, R. G., and Bell, B., "Visualization of extrastriatal dopamine D-2 receptors in the human brain," *Eur. J. Pharmacol.*, Vol. 223, pp. 105–107 (1992). The techniques for performing a PET assay may be found in Kessler, R. M., Votaw, J. R., de Paulis T., Bingham, D. R., Ansari, M. S., Mason, N. S., Holburn, G., Schmidt, D. E., Votaw, D. B., Manning, R. G. and Ebert, M. H., "Evaluation of 5-[$^{18}$F] Fluoropropylepidepride as a Potential PET Radioligand for Imaging Dopamine D2 Receptors," *Synapse*, Vol. 15, pp. 169–176 (1993); Wagner, Jr., H. N., "Positron Emission Tomography in Assessment of Regional Stereospecificity of Drugs," *Biochem. Pharmacol.*, Vol. 37, pp. 51–59 (1988).

By administration of a compound of this invention the biodistribution of the 5-HT-3 receptors in the brain can be reconstructed using computer assisted tomography. The fluorine-18 isotope is a positron emitter with a half-life of 1.8 h. The bromine-76 isotope is a positron emitter with a half-life of 16 h. The bromine-75 isotope is a positron emitter with a half-life of 1.6 h. The iodine-124 isotope is a positron emitter with a half-life of 4.2 d. Upon annihilation of an antimatter positron with normal matter, 5 KeV gamma radiation occurs which are powerful enough to be detected outside the body. The iodine-123 isotope is a gamma emitter with a half-life of 13 h. Other useful isotopes are bromine-77, iodine-125, and iodine,131.

Quantification of receptors in the living brain requires the pharmacokinetic behavior of the radioligands to be modeled in terms of measurable parameters, such as blood flow, uptake rates in brain compartments, and effective washout rates. The advantage of the compounds of the present invention is that they exhibit optimal apparent lipophilicity and receptor binding affinities for imaging of the 5-HT-3 receptors.

With reference to the formula (I) above, the radioactive halogen isotope may be positioned in either of the $R^1$, $R^2$, $R^3$ substituents. In order to use the invention in visualization of the serotonin S-3 receptor a suitable precursor is prepared and subjected to a radiochemical reaction. The crude reaction product is purified in a high performance liquid chromatographic column (HPLC), filtered through a sterile filter and administered intravenously to the individual subject. The visualization of the 5-HT-3 receptor subtype by means of receptor binding, autoradiography, single photon emission tomography (SPET), or positron emission tomography (PET) imaging techniques using appropriate fluorine, bromine, or iodine radioisotopes. Images of the localization of 5-HT-3 receptors can be collected in a SPET or PET scanner and reconstructed through data tomography.

The invention also provides a method of diagnosing an abnormal condition associated with altered 5-HT-3 receptor binding in an individual mammal comprising a. administering to an individual, or a sample from the individual, mammal the above radioactive compounds; b. detecting in the individual, or in the sample from the individual, a binding pattern between the compound and 5-HT-3 receptors; and, c. comparing the binding pattern in the sample from the individual, or in the individual, with a control binding pattern between the compound and 5-HT-3 receptors in a sample from normal individuals, a deviation from the control binding pattern indicating an abnormal condition associated with altered 5-HT-3 receptor binding. The invention contemplates that this "pattern" can be a pattern of 5-HT-3 location within an individual and/or a pattern of binding affinity at any particular location.

UTILITIES

Numerous utilities are set forth above. The present invention provides those skilled in the art with numerous presently available utilities. For example, the compounds and methods of the present invention can be used for the identification of the presence of 5-HT-3 receptors in a sample. This in turn can be used to identify or isolate a particular cell type expressing the receptor. For example, the compounds can be used to determine if cells within a given sample are eukaryotic by detecting binding to 5-HT-3 receptors. The compounds and methods of the present invention can be used for the identification of the location of 5-I-IT-3 receptors and these cells expressing the receptors in an individual. Such an identification can be performed either in vivo or in vitro.

The compounds can also be used for the treatment of abnormal conditions associated with a altered 5-HT-3 receptor binding, or other altered neurotransmitter receptor function regulated by 5-HT -3 receptor binding. Further, the compounds of the present invention can be used for the diagnosis of an abnormal condition associated with altered 5-HT-3 receptor binding.

The compounds can also be used to identify cells having a high number of receptors. This cell can then be used to screen for other compounds. Additionally, since the receptors occur only on cells in certain organs or locations in the body, the compounds cna be used to identify the source of a tissue sample. Likewise, the compounds could be used to detect the presence of human cellular contaminants in a sample.

The invention also provides numerous novel compounds with specific and unique binding affinity potencies ($K_i$), apparent lipophilicities ($logP_{app}$), and imaging contrast potentials ($1+50/K_iP_{app}$). Thus, the compounds provide a currently available tool with known reactive properties for the further elucidation of serotonin receptor binding patterns, diagnostics and therapeutic treatments for abnormal conditions associated therewith. The compounds of the present invention can thus be used in the treatment and diagnosis of the abnormal condition or disorder selected from the group consisting of gastric hypermotility, nausea, vomiting, bulemic, anorectic, and migraine conditions, and anxiety, personality, substance abuse, psychotic, schizophrenic, and cognitive disorders involving abnormal function or therapeutic modification of serotonin neurotransmission in peripheral organs or in the brain. These agents are also useful in the elucidation of the mechanism of action of antiserotonergic drugs and in monitoring the biodistribution and pharmacokinetics of new therapeutic agents. One skilled in the art will recognize these representative and other utilities of the present invention.

EXAMPLES

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °C. and pressure is at or near atmospheric.

Evaluation of the compounds of the present invention was performed by incubating the radiolabeled agent with tissue homogenates known to contain these receptors. By inhibiting the binding with various concentrations of competing ligands the relative potencies of unlabeled analogs were determined. The apparent lipophilicities of the compounds of the invention were estimated from the retention times in reverse-phase HPLC at pH 7.4. Finally, by calculating the inverse product of lipophilicity and inhibition constant a measure of their potential imaging contrasts in vivo between receptor-rich and receptor-poor regions were obtained. The method for evaluating the binding of the 5-HT-3 receptor was adopted from Kilpatrick, Jones, Tyers, Nature, Vol. 330, pp. 746–748 (1987), and Kilpatrick, G. J., Butler, A., Hagan, R. M., Jones, B. J., and Tyers, M. D., "[$^3$H] GR67330, a very high affinity ligand for 5-HT$_3$ receptors," Nauyn-Schmiedeberg's Arch Pharmacol., Vol. 342, pp. 22–30 (1990).

TABLE 1

Displacement of [$^{125}$I]-4 (Compound code TDP 960) binding in rat entorhinal cortex homogenates, the apparent lipophilicity at pH 7.4, and the calculated biodistribution contrast to the rat cerebellum uptake. $R^1$, $R^2$, and $R^3$ refer to the inventive formula I.

| Compound Code | Structure $R^1$ | $R^2$ | $R^3$ | $K_i$ (nM) (a) | log $P_{app}$ (b) | 1 + 50/ $K_i \cdot P_{app}$ (c) |
|---|---|---|---|---|---|---|
| 1. TDP 915 | I | H | H | 18 | 2.15 | 1.0 |
| 2. TDP 916 | I | CH$_3$ | H | 7.3 | 2.38 | 1.0 |
| 3. TDP 920 | I | CH$_2$F | H | 18 | 2.15 | 1.0 |
| 4. TDP 960 | I | H | OCH$_3$ | 1.5 | 1.87 | 1.5 |
| 5. TDP 1022 | I | CH$_3$ | OCH$_3$ | 2.7 | 2.19 | 1.2 |
| 6. TDP 917 | I | C$_2$H$_5$ | H | 16 | 2.81 | 1.0 |
| 7. TDP 921 | I | C$_2$H$_4$F | H | 24 | 2.44 | 1.0 |
| 8. TDP 918 | I | CH=CH$_2$ | H | 10 | 2.76 | 1.0 |
| 9. TDP 919 | I | CH$_3$(CH$_3$) | H | 5.6 | 2.52 | 1.0 |
| 10. TDP 922 | Br | H | H | 7.2 | 2.02 | 1.1 |
| 11. TDP 923 | Br | H | OCH$_3$ | 0.45 | 1.74 | 2.4 |
| 12. TDP 924 | Br | H | OC$_2$H$_5$ | 0.17 | 2.14 | 4.5 |
| 13. TDP 999 | Cl | H | OC$_2$H$_4$F | 0.20 | 1.70 | 8.7 |
| 14. TDP 994 | Cl | CH$_2$F | OCH$_3$ | 0.31 | 1.58 | 6.6 |
| 15. TDP 984 | Cl | CH=CH-I | OCH$_3$ | 0.29 | 2.58 | 1.6 |
| 16. TDP 1040 | Cl | H | I | 0.11 | 2.34 | 3.1 |
| 17. TDP 1059 | Cl | CH$_3$ | I | 0.40 | 2.47 | 1.3 |
| 18. TDP 1056 | Cl | CH$_2$F | I | 0.52 | 1.95 | 2.1 |
| 19. TDP 1050 | Cl | C$_2$H$_4$F | I | 1.25 | 2.38 | 1.1 |
| 20. TDP 1065 | Cl | C$_2$H$_5$ | I | 0.80 | 2.70 | 1.2 |
| 21. TDP 1046 | Cl | CH=CH$_2$ | I | 0.63 | 2.63 | 1.2 |
| 22. TDP 1053 | Cl | C≡CH | I | 0.70 | 2.57 | 1.2 |
| 23. TDP 1062 | Cl | CH$_3$(CH$_3$) | I | 0.72 | 2.45 | 1.3 |
| 24. TDP 1087 | F | H | H | 5.2 | 1.34 | 1.4 |
| 25. TDP 991 | I | H | OCH$_3$ | 19.0 | 1.87 | 1.0 |

(a) Calculated from IC$_{50}$ values of 0.64 nM [$^{125}$I]-4 ($K_D$ 1.5 nM).
(b) Extrapolated reverse phase capacity factors in MOPS buffer at pH 7.4.
(c) Adapted from Kessler's Rule: Log (target/cerebellum) = a log $B_{max}$/ $K_D$- log $P_{app}$ pH 7.4), Kessler et al., J. Nucl. Med. Vol. 32, pp. 1593–1600 (1990).
(d) $R^2$ is H except for compounds 9 and 23 where it is CH$_3$.
(e) Compound 25 is the R isomer, whereas all other values represent the S isomer.

TABLE 2

Specific binding of [$^{125}$I]-4 (Compound code TDP 960) and [$^{125}$I] iodozacopride in various regions of the rat brain. Zacopride is 5-chloro-4-amino-2-methoxy-N-(3-quinuclidinyl)benzamide. Iodozacopride is 5-iodo-4-amino-2-methoxy-N-(3-quinuclidinyl)benzamide.

| Brain region | [$^{125}$I]-4 Binding (fmol/mprotein)[a] | [$^{125}$I]iodozacopride binding (fmol/mg protein)[b] |
|---|---|---|
| Amygdala | 2.4 | 4.4 |
| Frontal cortex | 2.1 | 2.4 |
| Entorhinal cortex | 2.4 | 3.1 |
| Hippocampus | 1.3 | 2.1 |
| Hypothalamus | 0.9 | 1.1 |
| Striatum | 0.7 | 1.0 |
| Thalamus | 0.5 | N/A [c] |
| Cerebellum | 0.3 | 0.5 |

[a]Specific binding of 1.5 nM [$^{125}$I]-4 defined by 10 uM bemesetron (MDL 72222), assuming 10% protein concentration.
[b]Specific binding of 0.6 nM [$^{125}$I]iodozacopride defined by 1 uM ondansetron (GR 38032).
[c]Data not available.
[d]Data taken from Laporte et al., Synapse., Vol 10, pp. 271–281 (1992).

Displacement of 0.64 nM [$^{125}$I]-4 binding to homogenate of rat entorheal cortex in HEPES buffer by nine concentrations (0.3 to 300 nM) in triplicates of the known 5-HT-3 antagonists (S)-zacopride. quipazine. bemesetron (MDL-72222). and mianserin, and the dopamine D-2 receptor antagonist epidepride. and the two enantiomers of (see Example 1). [$^{125}$I]-4 was performed. Analysis of the specific binding (Lundon software) gave the results as shown in Table 3.

TABLE 3

| Compound | $K_i$(nM) | Lit. $K_i$(nM) | References |
|---|---|---|---|
| (S)-zacopride | 0.38 | 0.31 | Barnes et al., 1990 |
| quipazine | 0.48 | 1.4 | Kilpatrick et al., 1987 |
| Iodozacopride | ND(b) | 4.2 | Laporte et al., 1992 |
| bemestron | 18.3 | 36 | Emirit et al., 1993 |
| mianserin | 39 | 34 | Schmidt et al., 1989 |
| epidepride | 1035 | 1500 | Kessler et al., 1991 |
| (S)-4 | 1.35 | | |
| (R)-4 | 19 | | |

(a)The rank order and potencies of these agents in displacing [$^{125}$I]-4 binding are consistent with the assumption that the binding site is the 5-HT-3 receptor. Stereoselectivity of [$^{125}$I]-4 is 14.
(b)Data not available.

The compounds of the invention including the radioactive and non-radioactive compounds may be readily synthesized using techniques generally known to synthetic organic chemists. Suitable experimental methods for making and derivatizing benzamide compounds are generally described, for example, in the references cited in the Background section herein above, the disclosures of which are hereby incorporated by reference for their general teachings and for their synthesis teachings. Methods for making specific and preferred compounds of the present invention are described in detail in the Examples below.

Example I (S)-N-[3-(1-azabicyclo[2.2.2]octyl)]-2,3-dimethoxy-5-[$^{125}$I]iodobenzamide. (Radioactive analog of 4 (TDP 960) from Table I).

2,3-Dimethoxy-5-bromobenzoic acid was treated with $SOCl_2$ in toluene at 70° C. for 1 h, the solvent evaporated and the residual acid chloride condensed with (S)-3-aminoquinuclidine in $CH_2Cl_2$. The substituted bromobenzamide was purified by acid-base extractions and recrystallized as free base from isopropyl ether or as hydrochloride salt from acetone. (S)-2,3-Dimethoxy-5-bromo-N-(3-quinuclidinyl)benzamide was treated with bis(tributyltin) in triethylamine in the presence of tetrakis(triphenylphosphine) palladium(0). After refluxing for 18 h the solvent was evaporated and the excess reagents removed by passing the residue through a silica gel column in hexane-ethyl acetate-ethanol-14N ammonia (200:200:20:1). Fractions containing (S)-2,3-dimethoxy-5-tributyltin-N-(3-quinuclidinyl) benzamide were collected, the solvents evaporated, and the product redissolved in absolute ethanol (1 mg/mL). 10 uL of this solution was added to 5 mCi of Na$^{125}$I in 20 uL of 1N HCl followed by 10 uL of 2 mM chloramine-T in water. After 1 min 10 uL of 0.2N sodium metabisulfite was added and the product was purified in a reverse phase HPLC column (Rainin 5 um C18 4.5×250 mm) in 30% ethanol −0.1M phosphate buffer at pH 6.7. Radiochemical pure product of [125I]-4 (2.3 mCi in 3.6 mL at 1800 Ci/mmol) was obtained.

Example II (S)-N-[3-(1-Azabicyclo[2.2.2]octyl)]-5-chloro-3-methoxy-2-(1-[$^{125}$I]iodopropen-3-yl)oxy-benzamide. (Radioactive analog of 15 (TDP 984) from Table I).

Treatment of 3-methoxysalicylic acid with sulfuryl chloride in chloroform for 14 h at 23° C. gave 5-chloro-3-methoxysalicylic acid. This acid was treated with one equivalent of 18M sulfuric acid in refluxing methanol for 20 h to give methyl 5-chloro-3-methoxysalicylate. After recrystallization from isopropyl ether, the salicylate was treated with pargyline bromide in acetone in the presence of an excess of potassium carbonate. The resulting methyl 5-chloro-3-methoxy-2-(propyn-3-oxy)benzoate was hydrolyzed by heating for 1 h in ethanol containing an excess of 3N sodium hydroxide. 5-Chloro-3-methoxy-2-(propyn-3-oxy)benzoic acid was isolated by extraction with aqueous NaOH, neutralized with 12N HCl and extracted with ether. The acid was treated with $SOCl_2$ in toluene at 70° C. for 1 h, the solvent evaporated and the residual acid chloride condensed with (S)-3-aminoquinuclidine in $CH_2Cl_2$. The resulting substituted chlorobenzamide was purified by acid-base extractions and recrystallized as free base from isopropyl ether or as hydrochloride salt from acetone. (S)-5-Chloro-3-methoxy-2-(propyn-3-oxy)-N-(3-quinuclidinyl) benzamide was treated with tributyltin hydride in tetetrahydrofuran in the presence of azabisbutyronitrile. After refluxing for 18 h the solvent was evaporated and the excess reagents removed by passing the residue through a silica gel column in hexane-ethyl acetate-ethanol- 14N ammonia (200:200:20:1). Fractions containing (S)-5-chloro-3-methoxy-2-[(1-(tributyltin)propen-3-oxy]-N-(3-quinuclidinyl)benzamide were collected, the solvents evaporated, and the product redissolved in absolute ethanol (1 mg/mL). 10 uL of this solution was added to 5 mCi of Na$^{125}$I in 20 uL of 1N HCl followed by 10 uL of 2 mM chloramine-T in water. After 1 min 10 uL of 0.2N sodium metabisulfite was added and the product was purified in a reverse phase HPLC column (Rainin 5 um C18 4.5×250 mm) in 30% ethanol −0.1M phosphate buffer at pH 6.7. Radiochemical pure product of [$^{125}$I]-15 (1.0 mCi in 4.0 mL at 1800 Ci/mmol) was obtained.

Example III (S)-N-[3-(1-azabicyclo[2.2.2]octyl)]-5-chloro-2-(2-[$^{18}$F]fluoroethoxy)-3-iodobenzamide. (Radioactive analog of 18 (TDP 1056) from Table I).

5-Chlorosalicylic acid was treated with one equivalent of 18M sulfuric acid in refluxing methanol for 20 h to give methyl 5-chlorosalicylate. After recrystallization from isopropyl ether the salicylate was treated with the sodium salt of N-chloro-p-toluylsulfonamide in dimethylformamide in the presence of an excess of sodium iodide to give methyl 5-chloro-3-iodosalicylate. Treatment with 2-bromoethanol in refluxing acetone in the presence of an excess of potassium carbonate for 10 h gave methyl 5-chloro-3-iodo-2-(2-hydroxyethoxy)benzoate which was subsequently hydrolyzed in ethanol containing 3N NaOH to give 5-chloro-3-iodo-2-(2-hydroxyethoxy)benzoic acid. The acid was treated with 1,1-carbonyldiimidazole in DMF for 1 h, the resulting imidazole amide condensed with (S)-3-aminoquinuclidine. The resulting substituted chlorobenzamide was purified by acid-base extractions and the hydroxy group was protected by a toluenesulfonyl group. The tosylate can be reacted with 50 mCi of hydro[$^{18}$F]fluoric acid, prepared from H$_2$[$^{18}$O]O in an 11 MeV cyclotron and K$_2$CO$_3$-kryptofix[222] in acetonitrile for 20 min at 120° C. and purified by HPLC, to produce the radiochemical pure product of [$^{18}$F]-18.

Example IV (S)-N- [3-(1-Azabicyclo [2.2.2]octyl)]-5-chloro-3-[$^{125}$I]iodo-2-methoxybenzamide. (Radioactive analog of 16 (TDP 1040) from Table I).

3-Bromo-5-chloro-2-methoxybenzoic acid was treated with SOCl$_2$ in toluene at 70° C. for 1 h, the solvent evaporated and the residual acid chloride condensed with (S)-3-aminoquinuclidine in CH$_2$Cl$_2$. The substituted bromobenzamide was purified by acid-base extractions and recrystallized as free base from isopropyl ether or as hydrochloride salt from acetone. (S)-3-Bromo-5-chloro-2-methoxy-N-(3-quinuclidinyl)benzamide was treated with bis(tributyltin) in triethylamine in the presence of tetrakis (triphenylphosphine)palladium(0). After refluxing for 18 h the solvent was evaporated and the excess reagents removed by passing the residue through a silica gel column in hexane-ethyl acetate-ethanol-14N ammonia (200:200:20:1). Fractions containing (S)-2-methoxy-3-tributyltin-5-chloro-N-(3-quinuclidinyl)benzamide were collected, the solvents evaporated, and the product redissolved in absolute ethanol (1 mg/mL). 10 uL of this solution was added to 5 mCi of Na$^{125}$I in 20 uL of 1N HCl followed by 10 uL of 2 mM chloramine-T in water. After 1 min 10 uL of 0.2N sodium metabisulfite was added and the product was purified in a reverse phase HPLC column (Rainin 5 um C18 4.5×250 mm) in 30% ethanol −0.1M phosphate buffer at pH6.7. Radiochemical pure product [$^{125}$I]-16(2.3 mCi in 3.6 mL at 1800 Ci/mmol) was obtained.

Example V (R)-N-[3-1-Azabicyclo [2.2.2.]octyl]-5-iodo-2,3-dimethoxy-benzamide (25 (TDP-991) from Table I)

The free base of (R)-3-amino-quinuclidine was prepared by dissolving 0.40 g of the corresponding dihydrochloride (ALDRICH) in water (2 mL) and adding 10N NaOH (0.2 mL) followed by 100% ethanol (20 mL), filtration and evaporation of the solvent, repeated twice. 5-Iodo-2,3-dimethoxybenzoyl chloride (Yue et al., *J. Org. Chem.*, Vol. 56, p. 5451 (1991)) (0.86 g, 2.0 mmol) was condensed with (R)-3-amino-quinuclidine (0.26 g, 2.0 mmol) in DMF (15 mL). Yield of the substituted benzamide free base was 0.56 g (65%) as an oil, after purification on a short SiO$_2$ column (EtOAc—EtOH—NH$_4$OH, 50:10:1). Rotation: [α]$^{20}$D+13° (c2.4, MeOH). NMR(CDCl$_3$):δppm8.24 (bd, 1, NH), 7.99

(d, 1,6-CH), 7.30 (d, 1,4-CH), 4.17 (m, 1,3'-CH), 3.91 (s,3, OCH$_3$), 3.89(s,3, OCH$_3$), 3.44(dd, 1,2'-CH), 2.84(m,4,6'-CH$_2$,7'-CH$_2$), 2.59(dd, 1,2'-CH), 2.01(q, 1,4'-CH), 1.71(m, 4,5'-CH,8'-CH$_2$), 1.56(m, 1,5'-CH). The hydrochloride salt was prepared by dissolving the free base of TDP-991 (210 mg, 0.5 mmol) in acetone (3 mL) and adding 0.10 mL (0.5 mmol) of 5N HCl in 2-PrOH. Mp 187°–190° C.

Example VI (S)-N-[3-1-Azabicycyclo[2.2.2.]octyl)]5-chloro-3-methoxy-2-(1-iodopropen-3-yl)oxy-benzamide (15-TDP 984 from Table I).

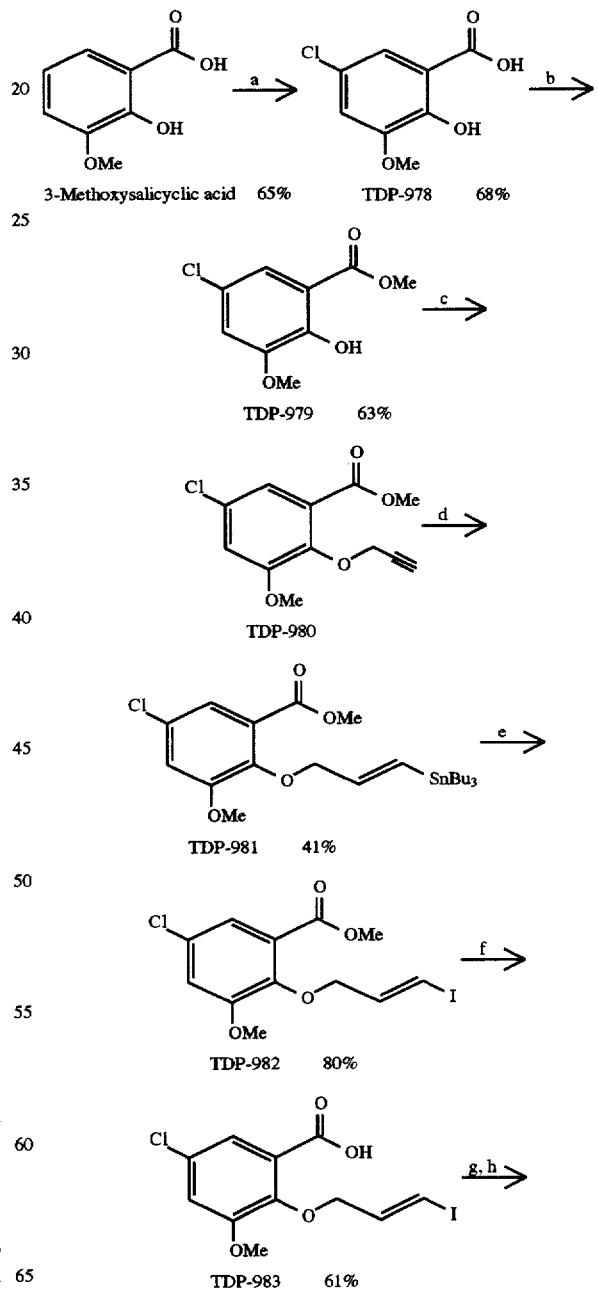

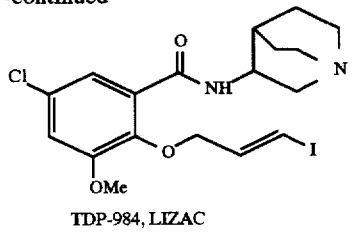

TDP-984, LIZAC

3-Methoxysalicylic acid (17 g. 0.10 mol) was treated with sulfuryl chloride (13.4 mL, 0.17 mol) in chloroform (300 mL) at 20° C. for 16 h. The precipitated product (TDP-978) was collected by filtration and recrystallized from i-Pr₂O (150 mL). Yield 13.2 g (65%). TDP 978 (10.1 g, 0.05 mol) was esterified by 18M sulfuric acid (2.0 ml, 0.036 mol) in methanol (250 ml). Yield 7.4 g (68%) of product (TDP 979) after recrystallization from 80% aqueous methanol (50 mL). Alkylation of TDP 979 (5.8 g, 0.027 mol) with 80% propargyl bromide (in toluene) (6.0 g, 0.040 mol) in the presence of an excess of $K_2CO_3$ in acetone (100 mL) gave 43 g (63%) of the desired product (TDP 980). Addition of tributyltinhydride (7.0 g, 0.024 mol) to TDP 980 (2.54 g, 0.01 mol) in dry THF (50 mL) and catalyzed by azabisisobutyronitrile (0.16 g, 0.001 mol) gave a 1 to 4 cis/trans mixture of the product (TDP 981) after refluxing for 21 h, evaporating the solvent and removed excess reagent by column chromatography in hexane-EtOAc, 3:1. TDP 981 (1.82 g, 3.3 mmol) was dissolved in $CHCl_3$ and iodine (1.0 g, 3.9 mmol) was added in portions at 20° C. After 2.5 h a solution of sodium bisulfite (1.2 g, 6.3 mmol) in 0.1N Hcl (30 mL) was added. Extraction of the product (TDP-982) with $CHCl_3$ (2×15 mL), drying and evaporation of the solvent gave cis/trans mixture of the product. TLC on silica (hexane-EtOAc, 3:1 ) showed two new spots at Rf0.45 and 0.38, respectively. The starting material (TDP-981) has $R_f$ 0.56. Crystallization twice from i-Pr₂O (35 mL) gave 0.52 g (41%) of pure trans isomer (TDP-982). Hydrolysis of the ester TDP-982 (0.5 g, 1.3 mmol) by 1N NaOH (5.0 mL, 5 mmol) in EtOH (5.0 mL) at 60° C. for 1.5 h gave the desired acid (TDP-983) in equivalent yield after dissolving in ether (25 mL) and extracting the product with 1N NaOH (2×15 mL). Neutralization with 12N HCl (3 mL, 36 mmol) and extraction with ether (2×25 mL) gave 0.37 g TDP-983 after recrystallization from i-Pr₂O (15 mL). These hydrolyzing conditions convert any cis-isomer present into the corresponding propargyl analogue (TDP-985). Conversion of TDP-983 (0.37 g, 1.0 mmol) to its corresponding acid chloride with thionyl chloride (0.5 g, 4.2 mmol) in toluene (8 mL) at 70° C. for 2 h and reacting the evaporated residue with (S)-3-aminoquinuclidine (0.4 g, 3.1 mmol) in DMF (5 mL) for 30 min gave the final product (TDP-984). Compound 15 was isolated and purified by dissolving in ether (15 mL) and washing with 1N NaOH (15 mL) to remove unreacted starting material. Extracting of the amine with 1N HCl (2×15 mL),neutralizing with 5N NaOH (6 mL), extracting with ether (2×15 mL), drying ($Na_2SO_4$), and evaporating the solvent gave 0.29 g (61%) of 15 as an oil. $[\alpha]^{20}D$-13° (c 0.7, $CHCl_3$). NMR-300 MHz ($CDCl_3$): δ8.05 (d,1H,NH), 7.63 (d,1H, 6-CH), 7.00 (d,1H, 4-CH), 6.79 (dt,1H, $CH_2CH=CH$-I), 6.61 (d, 1H, $CH_2CH=CH$-I), 4.47 (dt, 2H, $CH_2CH=CH$-I), 4.12 (m, 1H), 3.89 (s 3H, OMe), 3.42 (dd, 1H), 2.82 (m, 4H), 2.53 (dd, 1H), 1.96 (nm, 1H), 1.70 (m, 3H), 1.54 ppm (m, 1H).

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound of the formula I

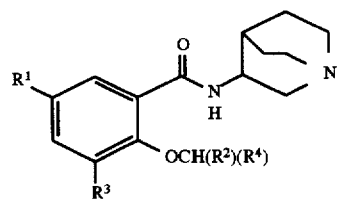

(I)

wherein, $R^1$ is fluorine, chlorine, bromine, iodine, alkyl, alkenyl, alkynyl, alkoxy, alkenoxy, or alkynoxy, $R^2$ and $R^3$ are independently hydrogen, fluorine, chlorine, bromine, iodine, alkyl, alkenyl, alkynyl, alkoxy, alkenoxy, or alkynoxy, wherein at least one of $R^1$, $R^2$, and $R^3$ is fluorine, bromine or iodine or is substituted with fluorine, bromine or iodine, and $R^4$ is H or lower alkyl, with the proviso that when $R^1$ is a halogen atom, then $R^2$, $R^3$ and $R^4$ are not hydrogen.

2. The compound of claim 1, wherein the carbon atom of the 3-quinuclidinyl moiety attached to the amide nitrogen has the S configuration.

3. The compound of claim 1, wherein the carbon atom of the 3-quinuclidinyl moiety attached to the amide nitrogen has the R configuration.

4. The compound of claim 1, wherein the alkyl, alkenyl, alkynyl, alkoxy, alkenoxy, and alkynoxy are lower alkyl, lower alkenyl, lower alkynyl, lower alkoxy, lower alkenoxy, and lower alkynoxy, respectively.

5. The compound of claim 1, wherein $R^1$ is fluorine, chlorine, bromine or iodine;

$R^2$ is H, lower alkyl unsubstituted or substituted with fluorine, bromine or iodine, or lower alkenyl unsubstituted or substituted with fluorine, bromine or iodine;

$R^3$ is fluorine, bromine or iodine or lower alkoxy unsubstituted or substituted with fluorine, bromine or iodine; and $R^4$ is H or a methyl group.

6. The compound of claim 1, wherein the carbon atom of the 3-quinuclidinyl moiety attached to the amide nitrogen has the S configuration, $R^4$ is H, and $R^1$ is I, $R^2$ is H, and $R^3$ is $OCH_3$;

$R^1$ is Cl, $R^2$ is $CH_2F$, and $R^3$ is $OCH_3$;

$R^1$ is Cl, $R^2$ is CH=CHI, and $R^3$ is $OCH_3$;

$R^1$ is Cl, $R^2$ is H, and $R^3$ is I;

$R^1$ is Cl, $R^2$ is $CH_2F$ and $R^3$ is I;

$R^1$ is Cl, $R^2$ is H, and $R^3$ is $OCH_2CH_2F$;

$R^1$ is F, $R^2$ is H, and $R^3$ is I; or $R^1$ is Cl, $R^2$ is H, and $R^3$ is $OCH_2CH=CHI$.

7. The compound of claim 1, wherein the carbon atom of the 3-quinuclidinyl moiety attached to the amide nitrogen has the R configuration, $R^4$ is H, and $R^1$ is I, $R^2$ is H, and $R^3$ is $OCH_3$;
$R^1$ is Cl, $R^2$ is $CH_2F$, and $R^3$ is $OCH_3$;
$R^1$ is Cl, $R^2$ is CH=CHI, and $R^3$ is $OCH_3$;
$R^1$ is Cl, $R^2$ is H, and $R^3$ is I;
$R^1$ is Cl, $R^2$ is $CH_2F$ and $R^3$ is I;
$R^1$ is Cl, $R^2$ is H, and $R^3$ is $OCH_2CH_2F$;
$R^1$ is F, $R^2$ is H, and $R^3$ is I; or
$R^1$ is Cl, $R^2$ is H, and $R^3$ is $OCH_2CH=CHI$.

8. A compound of the formula I

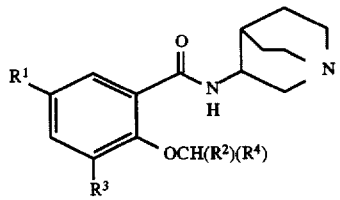

(I)

wherein, $R^1$ is fluorine, chlorine, bromine, iodine, alkyl, alkenyl, alkynyl, alkoxy, alkenoxy, or alkynoxy, $R^2$ and $R^3$ are independently hydrogen, fluorine, chlorine, bromine, iodine, alkyl, alkenyl, alkynyl, alkoxy, alkenoxy, or alkynoxy, wherein at least one of $R^1$, $R^2$, and $R^3$ is a radioactive isotope of fluorine, bromine or iodine or is substituted with a radioactive isotope of fluorine, bromine or iodine, and $R^4$ is H or lower alkyl.

9. The compound of claim 8, wherein the substitution of the radioactive isotope of fluorine, bromine or iodine is on the terminal portion of $R^2$ or $R^3$.

10. The compound of claim 8, wherein the radioactive isotope of fluorine, bromine or iodine is $^{18}F$, $^{75}Br$, $^{76}Br$, $^{77}Br$, $^{123}I$, $^{124}I$, $^{125}I$, or $^{131}I$.

11. The compound of claim 8, wherein the radioactive isotope of fluorine, bromine or iodine is $^{18}F$, $^{76}Br$, or $^{123}I$.

12. The compound of claim 8, wherein the carbon atom of the 3-quinuclidinyl moiety attached to the amide nitrogen has the S configuration.

13. The compound of claim 8, wherein the carbon atom of the 3-quinuclidinyl moiety attached to the amide nitrogen has the R configuration.

14. The compound of claim 8, wherein the alkyl, alkenyl, alkynyl, alkoxy, alkenoxy, and alkynoxy are lower alkyl, lower alkenyl, lower alkynyl, lower alkoxy, lower alkenoxy, and lower alkynoxy, respectively.

15. The compound of claim 8, wherein $R^1$ is fluorine, chlorine, bromine or iodine or a radioactive isotope of fluorine, bromine or iodine;

$R^2$ is H, lower alkyl unsubstituted or substituted with a non-radioactive isotope of fluorine, bromine or iodine or a radioactive isotope of fluorine, bromine or iodine, or lower alkenyl unsubstituted or substituted with a non-radioactive isotope of fluorine, bromine or iodine atom or a radioactive isotope of fluorine, bromine or iodine;

$R^3$ is a non-radioactive isotope of fluorine, bromine or iodine or a radioactive isotope of fluorine, bromine or iodine or lower alkoxy unsubstituted or substituted with a non-radioactive isotope of fluorine, bromine or iodine or a radioactive isotope of fluorine, bromine or iodine; and $R^4$ is H or a methyl group.

16. The compound of claim 8, wherein the carbon atom of the 3-quinuclidinyl moiety attached to the amide nitrogen has the S configuration, $R^4$ is H, and $R^1$ is I, $R^2$ is H, and $R^3$ is $OCH_3$;
$R^1$ is Cl, $R^2$ is $CH_2F$, and $R^3$ is $OCH_3$;
$R^1$ is Cl, $R^2$ is CH=CHI, and $R^3$ is $OCH_3$;
$R^1$ is Cl, $R^2$ is H, and $R^3$ is I;
$R^1$ is Cl, $R^2$ is $CH_2F$ and $R^3$ is I;
$R^1$ is Cl, $R^2$ is H, and $R^3$ is $OCH_2CH_2F$;
$R^1$ is F, $R^2$ is H, and $R^3$ is I; or
$R^1$ is Cl, $R^2$ is H, and $R^3$ is $OCH_2CH=CHI$;

wherein at least one of I or F is radioactive.

17. The compound of claim 8, wherein the carbon atom of the 3-quinuclidinyl moiety attached to the amide nitrogen has the R configuration, $R^4$ is H, and $R^1$ is I, $R^2$ is H, and $R^3$ is $OCH_3$;
$R^1$ is Cl, $R^2$ is $CH_2F$, and $R^3$ is $OCH_3$;
$R^1$ is Cl, $R^2$ is CH=CHI, and $R^3$ is $OCH_3$;
$R^1$ is Cl, $R^2$ is H, and $R^3$ is I;
$R^1$ is Cl, $R^2$ is $CH_2F$ and $R^3$ is I;
$R^1$ is Cl, $R^2$ is H, and $R^3$ is $OCH_2CH_2F$;
$R^1$ is F, $R^2$ is H, and $R^3$ is I; or
$R^1$ is Cl, $R^2$ is H, and $R^3$ is $OCH_2CH=CHI$;

wherein at least one of I or F is radioactive.

18. A composition for the treatment of abnormal conditions or disorders associated with altered 5-HT-3 receptor binding, or with altered neurotransmitter receptor function regulated by 5-HT-3 receptors, in an individual comprising a therapeutically effective amount of the compound of claim 1 and a pharmaceutically acceptable carrier.

19. The composition of claim 18, wherein the amount of the compound is an amount to treat the abnormal condition or disorder is selected from the group consisting of gastric hypermotility, nausea, vomiting, bulemic, anorectic, and migraine conditions, and anxiety, personality, substance abuse, psychotic, schizophrenic, and cognitive disorders.

* * * * *